United States Patent [19]

Poncet et al.

[11] Patent Number: 5,254,130
[45] Date of Patent: Oct. 19, 1993

[54] SURGICAL DEVICE

[75] Inventors: Philippe Poncet; Karl van Dyk, both of Fremont, Calif.

[73] Assignee: Raychem Corporation, Menlo Park, Calif.

[21] Appl. No.: 867,649

[22] Filed: Apr. 13, 1992

[51] Int. Cl.$^5$ .............................................. A61B 17/28
[52] U.S. Cl. .................................. 606/206; 606/205; 606/207; 606/210; 606/167; 606/170; 606/174; 128/751
[58] Field of Search ............... 128/751, 752, 753, 754, 128/772; 604/164, 165, 171; 606/106, 151, 170, 174, 205, 206, 210, 211

[56] References Cited

U.S. PATENT DOCUMENTS

| | | |
|---|---|---|
| 2,114,695 | 4/1938 | Anderson . |
| 2,137,710 | 11/1938 | Anderson . |
| 2,670,519 | 3/1954 | Recklitis . |
| 3,404,677 | 10/1968 | Springer . |
| 3,958,576 | 6/1976 | Komiya ............................ 606/174 |
| 4,200,111 | 4/1980 | Harris ................................ 128/751 |
| 4,203,444 | 5/1980 | Bonnell et al. . |
| 4,665,906 | 5/1987 | Jervis . |
| 4,723,545 | 2/1988 | Nixon et al. . |
| 4,882,777 | 11/1989 | Narula . |
| 4,926,860 | 5/1990 | Stice et al. . |
| 4,945,920 | 8/1990 | Clossick ............................ 606/205 |

OTHER PUBLICATIONS

U.S. Specification (Ser. No. 07/843,775, dated Feb. 28, 1992, Inventors Middleman et al).

Primary Examiner—C. Fred Rosenbaum
Assistant Examiner—Noelle Kent Gring
Attorney, Agent, or Firm—Herbert G. Burkard; Sheri M. Novack

[57] ABSTRACT

A surgical device comprising
(a) a tubular housing having a longitudinal bore extending therethrough,
(b) a first elongate member extending through the longitudinal bore of the housing, and having a proximal and a distal segment, where at least part of the distal segment comprises an elastic material, especially a super elastic material, and wherein the distal segment assumes a first shape when extended from the longitudinal bore, and a second shape when withdrawn into the bore,
(c) a second elongate member also having a proximal and a distal segment, the second elongate member extending substantially parallel to the first elongate member so that it is moved by the first elongate member, when the first elongate member changes from its first to its second shape and vice versa, the second elongate member being rotatable relative to, and substantially about, the axis of the first elongate member, and
(d) an operating head secured to the distal segment of the second elongate member so that it
   (i) is moved with the second elongate member when the first elongate member changes from its first to its second shape and
   (ii) can be rotated by the second elongate member substantially about the axis of the first elongate member.

18 Claims, 2 Drawing Sheets

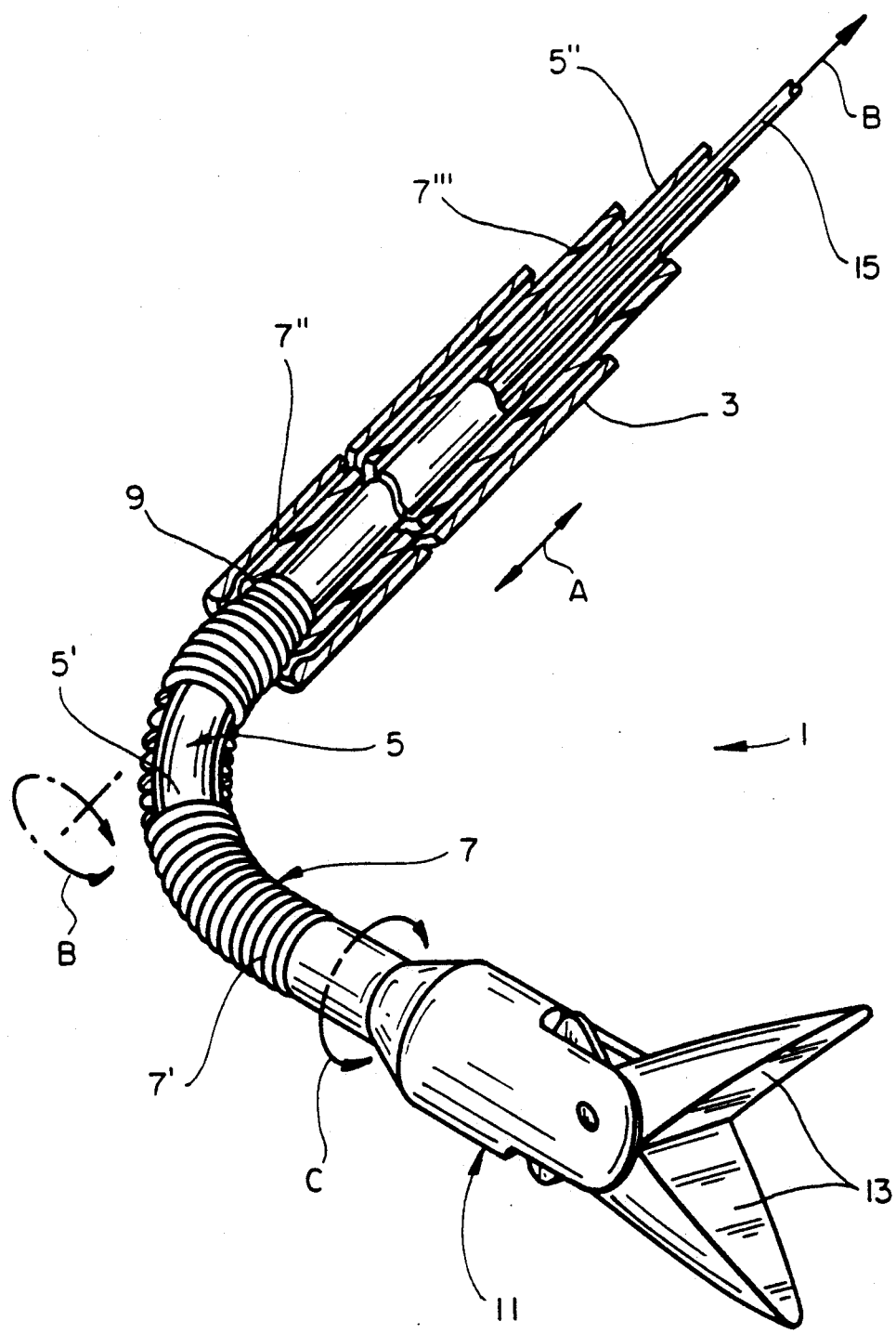
FIG_1

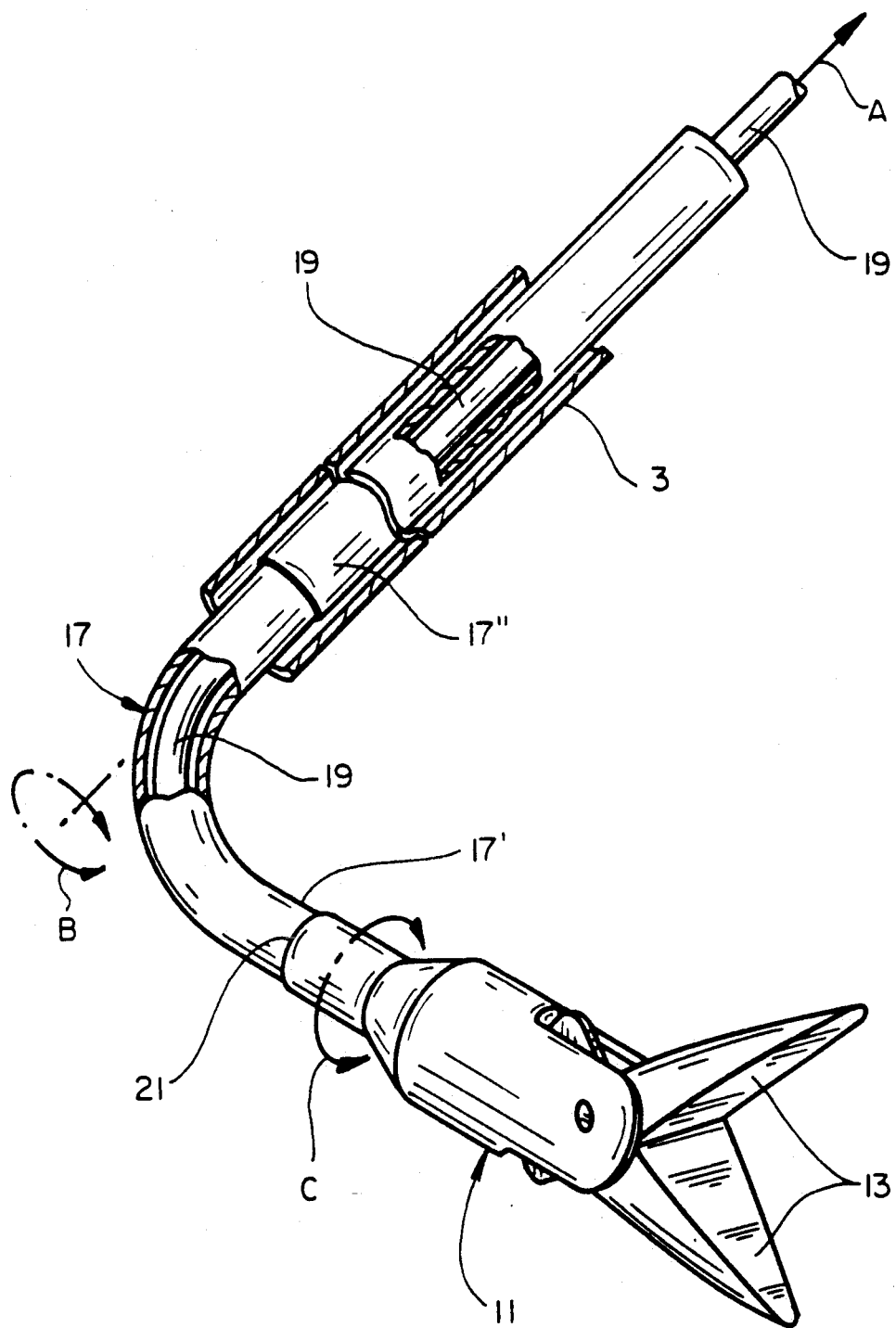
FIG_2

SURGICAL DEVICE

TECHNICAL FIELD

This invention relates to surgical devices, particularly to remotely operated surgical devices for use in least invasive surgical (LIS) techniques.

BACKGROUND OF THE INVENTION

LIS techniques are in contrast to open surgical techniques. They include operation through natural ducts within the body (endoscopy) and operation through one or more relatively small openings made by the surgeon in the patient's body (percutaneous techniques), for example laparoscopic surgery involving making small openings in the patient's abdominal wall, and arthroscopic surgery involving making small openings in a joint region. Advantages of LIS, compared to open surgery, are lower morbidity rates, shorter patient recovery times and lower costs of the procedure.

Surgical devices used in LIS are remotely operated. Typically devices are inserted into the patient's body, the operating head of the device is projected beyond the distal end of the housing, and this operating head is then activated by the surgeon from the proximal end of the device.

Simple, known LIS surgical devices use, for example, flexible steel wires which spring apart when extended from the distal end of a tube and which can be brought together again on withdrawal back into the tube. Examples of such devices are described, in U.S. Pat. Nos. 2,114,695, 2,137,710, 2,670,519, and 3,404,677.

Numerous LIS surgical devices incorporating a variety of special materials, including shape memory alloys are also known. U.S. Pat. No. 4,926,860 to Stice et al, issued 22 May 1990, for example, describes an arthroscopic procedure using a curved cannula and a normally straight shape memory alloy probe. The curved cannula facilitates access to parts of the joint, and bends the probe as it passes therethrough. However when the probe exits from the distal end of the cannula it adopts its normal straight configuration.

Also U.S. Pat No. 4,665,906 to Jervis discloses medical devices which make use of the pseudoelastic (SIM) properties of certain shape memory alloys. SIM pseudoelastic properties and their advantages are discussed in more detail later in this specification.

LIS devices incorporating elastic materials, including pseudoelastic shape memory alloys are also known, as described in U.S. Ser. No. 843,775 pending to the Applicant, filed Feb. 28, 1992. One embodiment described therein is an apparatus which enables passage of a ligature around a bone or other body member, or grasping of such a body member without requiring the surgical instrument to be swept over a wide angle of motion. The apparatus includes a cannula and a pseudo elastic member within the cannula. An example given is for the cannula to be straight and for the pseudo elastic member to adopt a curved configuration when extended from the cannula sufficient to grasp and manipulate a body structure. Another embodiment describes delivery of a needle to a surgical site through a curved arc by using a pseudo elastic needle. Other similar examples all involving the extension of pseudo elastic members from a housing to manipulate matter are described in U.S. Ser. No. 843,775. Other examples where the advantages of the pseudo elastic members in accessing difficult spaces within the patient's body would be evident to the man skilled in the art. The disclosure of U.S. Ser. No. 843,775 is incorporated herein by reference.

LIS surgical devices involving rotation of a knife are also known. For example, U.S. Pat. No. 4,723,545 to Nixon and Mombrimie, issued 9th Feb. 1988 describes a surgical instrument suited for arthroscopic surgery comprising a blade mounted in a tubular body portion so that it can project beyond the body portion and so that is can oscillate with respect to the body portion. This oscillation of the blade facilitates the cutting process, nothwithstanding the toughness or cut resistance of the tissue or the like which is to be repaired. Also U.S. Pat. No. 4203444 to Bonnell et al, issued on 20th May 1980 describes a surgical instrument for use in closed surgery of the knee, comprising an outer tube containing an inner tube. The inner tube is provided with shearing edges which form a blade. The inner tube can rotate within the outer tube at speeds in the range of 100-200 rpm, and a vacuum may be provided to withdraw the material sheared by the blade.

A problem experienced with the LIS and other surgical devices used in the past is in achieving movement in three dimensions to precisely access the desired surgical site, and to move the surgical instrument in the desired directions once it is at the desired surgical site.

U.S. Pat. No. 4882777 to Narula issued 21 Nov. 1989 provides some three dimensional character in the positioning of a catheter. This describes a catheter which is sufficiently resilient to deform to a linear configuration for insertion through a narrow tube, but which has a complex curvature that is not limited to a single plane. This skews the extreme distal end of the catheter relative to a straight portion and a first curved portion of the catheter, allowing automatic positioning of the distal end adjacent the desired internal location. However the automatic positioning is still to a desired predetermined position defined by the complex curvature of the catheter.

It is an object of the present invention to overcome the deficiencies of the prior art surgical devices, in particular the prior art LIS surgical devices.

It is a particular object of the present invention to provide a surgical device which allows another degree of freedom of movement to an operator of the surgical device, outside a single plane. In particular it is an object of the invention to provide a device in which the operator of the surgical device can deliver the head of the surgical device to a surgery site along a first path, which may be any direction of path but is typically a curved path in a single plane, and can then rotate the head of the device in another dimension, for example around the axis defined by the direction of the first path.

It is a further object of the present invention to provide a surgical device that is small in transverse dimensions, and is thus suitable for use in LIS techniques.

SUMMARY OF THE INVENTION

The present invention provides a surgical device comprising
(a) a tubular housing having a longitudinal bore extending therethrough,
(b) a first elongate member extending through the longitudinal bore of the housing, and having a proximal and a distal segment, where at least part of the distal segment comprises an elastic material (as hereinafter defined), and wherein the distal segment assumes a first shape when extended from the longitudinal bore, and a second shape when withdrawn into the bore, (c) a second elongate member also having a proximal and a distal segment, the second elongate member extending substantially parallel to the first elongate member so that it is moved by the first elongate member, when the first elongate member changes from its first to its second shape and vice versa, the second elongate member being rotatable relative to, and substantially about, the axis of the first elongate member, and (d) an operating head secured to the distal segment of the second elongate member so that it
  (i) is moved with the second elongate member when the first elongate member changes from its first to its second shape and
  (ii) can be rotated by the second elongate member substantially about the axis of the first elongate member.

BRIEF DESCRIPTION OF THE DRAWINGS

FIGS. 1 and 2 are partly cut away, partly sectional and partly perspective views of first and second embodiments of surgical device according to the invention.

DETAILED DESCRIPTION OF THE INVENTION

The present invention requires at least part of the distal segment of the first elongate member to comprise an elastic material.

Any elastic material may be used in some of the embodiments of this invention, but it is generally preferred to use a pseudoelastic material. Many different materials exhibit pseudoelasticity and can be used in any embodiment of this invention. It is preferred to use a pseudoelastic shape memory alloy.

The term "elastic material" is used herein to mean a material that has spring-like properties, that is, it is capable of being deformed by an applied stress and then springing back, or recovering, to or toward its original unstressed shape or configuration when the stress is removed. The elastic material is preferably highly elastic. The material can be polymeric or metallic, or a combination of both. The use of metals, such as shape memory alloys, is preferred. Shape memory alloys that exhibit pseudoelasticity, in particular superelasticity, are especially preferred. The elastic materials herein exhibit greater than 1% elastic deformation, more generally greater than 2% elastic deformation. Preferably, the elastic materials herein exhibit greater than 4% elastic deformation, more preferably greater than 6% elastic deformation.

Preferably, the elastic member is at least partially formed from a pseudoelastic material, such as a shape memory alloy that exhibits pseudoelasticity. Shape memory alloys which exhibit superelasticity (also referred to in the literature as non-linear pseudoelasticity), are especially preferred.

U.S. Pat. No. 4,935,068 to Duerig, which is commonly assigned with the present application and incorporated herein by reference, teaches the fundamental principles of shape memory alloys. Some alloys which are capable of transforming between martensitic and austenitic phases are able to exhibit a shape memory effect. The transformation between phases may be caused by a change in temperature. For example, a shape memory alloy in the martensitic phase will begin to transform to the austenitic phase when its temperature rises above $A_S$ and the transformation will be complete when the temperature rises above $A_f$. The forward transformation will begin when the temperature drops below $M_S$ and will be complete when the temperature drops below $M_f$. The temperatures $M_S$, $M_f$, $A_S$, and $A_f$ define the thermal transformation hysteresis loop of the shape memory alloy.

Under certain conditions, shape memory alloys exhibit pseudoelasticity, which does not rely on temperature change in order to accomplish shape change. A pseudoelastic alloy is capable of being elastically deformed far beyond the elastic limits of conventional metals.

The property of pseudoelasticity of certain shape memory alloys, which preferably is used in the devices of this invention, is the subject of a paper entitled "An Engineer's Perspective of Pseudoelasticity", by T. W. Duerig and R. Zadno, published in Engineering Aspects of Shape Memory Alloys, page 380, T. W. Duerig, K. Melton, D. Stoeckel, and M. Wayman, editors, Butterworth Publishers, 1990 (proceedings of a conference entitled "Engineering Aspects of Shape Memory Alloys", held in Lansing, Mich. in August 1988). As discussed in the paper, the disclosure of which is incorporated herein by reference, certain alloys are capable of exhibiting pseudoelasticity of two types.

"Superelasticity" arises in appropriately treated alloys while they are in their austenitic phase at a temperature which is greater than $A_S$ and less than $M_d$ ($A_S$ is the temperature at which, when a shape memory alloy in its martensitic phase is heated, the transformation to the austenitic phase begins, and $M_d$ is the maximum temperature at which the transformation to the martensitic phase can be induced by the application of stress). Superelasticity can be achieved when the alloy is annealed at a temperature which is less than the temperature at which the alloy is fully recrystallized. Alternative methods of creating superelasticity in shape memory alloys, such as solution treating and aging, or alloying, are also discussed in "An Engineer's Perspective of Pseudoelasticity", referenced above. An article may be provided with a desired configuration by holding it in that configuration during annealing, or during solution treatment and aging. An article formed from an alloy which exhibits superelasticity can be deformed substantially reversibly by 11% or more. In contrast, "linear pseudoelasticity", is believed not to be accompanied by a phase change. It is exhibited by shape memory alloys which have been cold worked or irradiated to stabilize the martensite, but have not been annealed in the manner discussed above. An article formed from an alloy which exhibits linear pseudoelasticity can be deformed substantially reversibly by 4% or more. The treatment of shape memory alloys to enhance their pseudoelastic properties is also discussed in above-mentioned U.S. Pat. No. 4,935,068 to Duerig, incorporated herein by reference.

While the alloy that is used in the devices of this invention may exhibit either linear pseudoelasticity or superelasticity (which is sometimes referred to as non-linear pseudoelasticity), or pseudoelasticity of an intermediate type, it is generally preferred that it exhibit superelasticity because of the large amount of deformation that is available without the onset of plasticity. U.S. Pat. No. 4,665,906 to Jervis, which is commonly assigned with the present application and is incorporated herein by reference, teaches the use of pseudoelastic shape memory alloys in medical devices.

The pseudoelastic material will be selected according to the characteristics desired of the article. When a shape memory alloy is used, it is preferably a nickel titanium based alloy, which may include additional elements which might affect the yield strength that is available from the alloy or the temperature at which particular desired pseudoelastic characteristics are obtained. For example, the alloy may be a binary alloy consisting essentially of nickel and titanium, for example 50.8 atomic percent nickel and 49.2 atomic percent titanium, or it may include a quantity of a third element such as copper, cobalt, vanadium, chromium or iron. Alloys consisting essentially of nickel, titanium and vanadium, such as disclosed in U.S. Pat. No. 4,505,767, the disclosure of which is incorporated herein by reference, are preferred for some applications, particularly since they can also exhibit superelastic properties at or around body temperatures, and because they are stiffer and/or can store more elastic energy. Copper based alloys may also be used, for example alloys consisting essentially of copper, aluminum and nickel; copper, aluminum and zinc; and copper and zinc.

An article exhibiting superelasticity can be substantially reversibly deformed, by as much as eleven percent or more. For example, a 1.00 meter length of superelastic wire may be stretched to 1.11 meters in length, wherein its alloy will undergo a phase change to at least a partially more martensitic phase known as stress-induced-martensite. Upon release of the stress, the wire will return substantially to its 1.00 meter length, and its alloy will, correspondingly, return at least substantially toward its more austenitic phase. By way of contrast, a similar wire of spring steel or other conventional metal may only be elastically stretched approximately one percent, or to 1.01 meter in length. Any further stretching of the conventional wire, if not resulting in actual breakage of the wire, will result in a non-elastic (plastic) transformation such that, upon relief of the stress, the wire will not return to its original length. Linear pseudoelastic and superelastic materials may also be bent, twisted, and compressed, rather than stretched, to a far greater degree than conventional metals.

It is believed that the superelastic property is achieved by phase transformation within the alloy, rather than by the dislocation movements which occur during the plastic deformation of ordinary metals. A superelastic material may be deformed and released thousands of times, without being subject to breakage due to the metal fatigue which limits the number of deformation cycles which an ordinary metal may undergo without failure.

Shape memory alloys have a special feature which is beneficial for certain of the embodiments of this invention. As a superelastic shape memory alloy is increasingly deformed from its unconstrained shape, some of its austenitic phase changes into stress-induced-martensite. The stress/strain curve presents a plateau during this phase change. This means that while the alloy undergoes this phase change, it can deform greatly with only minimal increases in loading. Therefore, elements comprising superelastic shape memory alloys have a built-in safety feature. These elements can be designed (using appropriately treated alloys and appropriate dimensions) such that when they are loaded beyond a certain amount, the elements will tend to deform with a concomitant austenite to stress-induced-martensite phase change, instead of merely presenting a greater resistance or force with limited deformation to the load, which is seen with conventional metals.

Just as the stress strain curves of shape memory alloys present a plateau upon loading, they also present a plateau in the stress strain curve upon unloading. Unloading occurs when an element made of superelastic shape memory alloy is permitted to revert from a significantly deformed shape toward its original unstressed shape. Because of the plateau, such an element can maintain an almost constant force during much of the unloading cycle until just before it is completely unloaded.

In one embodiment of the invention therefore the elastic material is selected to have an $A_s$ lower than ambient temperature, so that when the distal segment of the first elongate member is extended from the bore of the tubular housing it adopts its original (i.e. previous and predetermined) shape. For example the tubular housing may be straight, and the first member be constrained to a generally straight configuration therein, but adopt a curved configuration when extended from the end of the housing.

In addition, the surgical device of the present invention comprises a second elongate member that is rotatable relative to the first elongate member, and which carries an operating head at its distal end which can similarly be rotated by the second elongate member about the first elongate member.

The operating head may comprise for example a laparoscopic needle driver, scissors, forceps, dissectors, graspers, or the like, or a holding means for such instruments. The invention allows the operator to deliver the operating head along a predetermined path, and then allows an extra degree of freedom of movement of the operating head, by rotation. Thus the flexibility and opportunity of direction of movement of the operating head achieved by the combination of the initial elastic behavior of the first elongate member, and the rotation achievable by the second elongate member is greatly increased.

Any suitable arrangement whereby the second elongate member is movable by the first elongate member, and is additionally rotatable therearound is within the scope of the present invention. In one embodiment at least part of at least the distal segment of the second elongate member is tubular and surrounds at least part of the first elongate member. Preferably the surrounding tubular second member is flexible. This construction means that as the first member changes from its first to second shape, the second member will move with the first member to follow that shape change. Preferably the second elongate member is sufficiently flexible that it can be moved by the first member with little or no resistance from its own structure. As examples, at least part of at least the distal segment of the second member may comprise any of the following: a circumferentially corrugated tube, a spring, a fibrous braided tube, a flexible polymeric tube, or a polymeric braided tube. Where a circumferentially corrugated configuration is used this can provide the flexibility.

The proximal segment of the second elongate member is preferably continuous with its distal segment, and may take the same or a different form. In use the proximal segment may remain at all times within the housing, therefore flexibility may not be required or desired for the proximal segment. This is especially true if the housing is linear. Preferably the proximal segment of the second elongate member extends beyond the proximal end of the housing. This allows the operator of the surgical device to handle the proximal segment to rotate the second member around the first from the proximal end of the device. For example where the surgical device is used in an LIS technique it allows rotation of the operating head of the device to be effected by rotation by the operator of the second member, at the proximal end of the device, outside of the patient's body.

The distal end of the second member, which in use, enters into, or may enter into, contact with the internal parts of the patient's body may comprise a polymeric material. Suitable materials would be apparent to the man skilled in the art.

In a different embodiment of the invention at least part of at least the distal segment of the second elongate element extends within at least part of at least the distal segment of the first elongate element. In other words, the position of the first and second elongate members are interchanged compared to the above described embodiment. For example at least the distal segment of the first elongate element (which comprises an elastic material) may define a tube. It may be in the form of a tube, or it may, for example, comprise elongate bars and tie bars which together define the periphery of a tube. Provided the distal segment can behave elastically as defined, it can take any suitable form. The second elongate member used in combination with the tubular first elongate member may also be in the form of a tube, or may be in the form of a cable, for example of the type used in a speedometer or the like. This cable can pass through the first elongate member, and can act on the operating head remotely from the proximal end of the device. In this embodiment the proximal segment of the first elongate member is preferably also tubular and is preferably secured to, or integral with, the distal segment thereof so relative rotation therebetween is prevented. The distal segment comprises elastic material. The proximal segment may or may not comprise elastic material. For cost reasons it may not do.

The operating head of the surgical device may take any suitable form depending on the nature of the use of the device. For multi-functionability the head may comprise a clevis or the like, i.e. a holding means (for example in the case of a clevis, a U-shaped holding means) to which specific instruments can be secured, eg jaws of a clamp or forceps, a needle for suturing, blades of, for example, scissors or the like. Thus such instruments may be directly attached to the second elongate member of the device, or they may be secured in a holding means such as a clevis or the like, which is itself secured to the second elongate member.

Where the instrument at the operating head needs to be activated e.g. where it comprises mating jaws or mating blades of clamps, forceps or scissors, then elongate activating means may pass within, or along the outside of, the outer of the first and second elongate member.

At least the distal segment of the first elongate element preferably comprises a shape memory alloy, preferably a pseudoelastic, especially a superelastic alloy. In use, the first and second elongate members are preferably constrained at ambient temperature, within the housing in their stress induced martensitic state. When the device is inserted into the body, the first and second elongate members are then moved longitudinally relative to the tube so that the distal segments thereof project beyond the end of the housing. The distal segment of the first elongate member is then unstressed, and being above its $A_s$ temperature reverts to its austenitic state, and hence to its original austenitic shape. As explained above very large shape changes can be achieved in this way. Typically a first pseudoelastic member deformed within a straight housing may adopt a curved configuration on exiting the housing. The second member (which as explained above preferably extends within the first member, or is itself tubular and surrounds the first member) follows the path of the first member, and is preferably flexible to enable it to do this. The second member can then or simultaneously be rotated about the first member to rotate the operating head.

According to the invention surgical devices having small transverse dimensions can be made that are nonetheless versatile in application, making them particularly suitable for LIS techniques. Preferably devices in which the housing (containing both first and second members) has a transverse dimension of less than 10 mm preferably less than 7 mm, especially about 5 mm are used. Preferably the housing is substantially cylindrical and the transverse dimension is its diameter.

Referring now to the drawings, these show, by way of example only, embodiments of the present invention.

Referring to FIG. 1, a first surgical device suitable for use in LIS technique according to the invention is designated generally by the reference numeral 1. It comprises a tubular generally straight housing 3, and first and second elongate members 5 and 7 respectively extending through the housing 3. For simplicity we shall term the first elongate member 5 the "bending member 5" and the second elongate member 7 the "rotating member 7". Both the bending member 5 and the rotating member 7 are shown deployed beyond the distal end of the surgical device. This is the position they would be deployed within the patient's body. Both can be retracted within the housing 3 by moving them longitudinally relative to the housing 3 in the direction indicated by arrow A. Typically they would be retracted within the housing for insertion into the patient's body.

The bending member 5 comprises a distal segment 5' and a proximal segment 5". The distal segment 5' comprises a tubular, pseudoelastic, preferably superelastic memory metal alloy. The proximal segment of the bending member 5 is also tubular. It is secured to the pseudoelastic segment, but does not itself exhibit memory behaviour. It is fixed relative to the housing 3 so it cannot be rotated relative to housing 3. The distal segment 5' of the bending member 5 can be deformed into a straight configuration by the action of the operator withdrawing it within housing 3 in the direction of arrow B in the Figure. When deployed outside the housing (as shown) by the operator moving it in the direction opposite to direction B it automatically adopts its previous "remembered" configuration, in this case a curved configuration as shown. Thus bending in a single plane (the plane of the paper), as depicted in FIG. 1 by arrow C is achieved by this bending member 5.

The second elongate member or rotating member 7 also comprises a distal segment 7' and a proximal segment 7" as shown. Both segments 7' and 7" are tubular and polymeric and surround corresponding segments 5' and 5" of the bending member. Segment 7' is circumferentially corrugated to render it flexible so that is easily bent with the bending segment 5' when deployed outside the housing 3. The proximal segment 7" is not corrugated since it does not need to bend. It is fixed to the corrugated distal segment 7' at point 9. The proximal segment 7" projects beyond the housing 3, and this projecting portion (designated 7"') can be rotated by the operator (outside the patient's body), causing simultaneous rotation of the corrugated distal segment 7'. The direction of rotation is depicted by the arrow C in FIG. 1. It is about the axis of bending member 5. The rotating member 7 is not fixed relative to bending member 5, and therefore can rotate around member 5.

The operating head of the surgical device is a holding means in the form of a clevis 11. In the U-bend of the clevis 11 clamping jaws 13 are pivoted.

The clevis 11 is secured to the corrugated segment 7' of the rotating member 7, so that when the projecting proximal segment 7"' of that member is rotated by the operator outside the housing and the patient, the torque is transmitted by the segment 7" and by the corrugated segment 7' to the clevis 11, so that rotation of the clevis 11 occurs around its own axis and around the bending member 5'. Transmission of the rotating torque to the clevis occurs in this way, by the corrugated segment 7', regardless of whether the bending and rotating members 5 and 7 are deployed fully, partly or not at all from the housing, ie regardless of whether the members 5 and 7 are straight or curved.

During an operation, the clevis can therefore be steered into the correct position by action of the first bending member 5 and then rotated by the operator by the rotating member 7, giving an extra degree of freedom for the operator of the instrument, ie three dimensional control is achieved.

The device 1 is also provided with an activating shaft 15 passing through the device which can activate the jaws 13. Any known mechanical linkage can be used to effect this activation.

The housing 3 may be any suitable dimension. It is preferably cylindrical with a diameter less than 5 mm.

FIG. 2 shows an alternative form of surgical device. Like parts to FIG. 1 are given identical reference numbers to FIG. 1. In this case the first elongate member 17 is referred to as the bending member 17. This is in the form of a tube surrounding the second elongate member, which is referred to as the rotating member 19. The rotating member 19 is in the form of a cable extending through the bending member 17. As in FIG. 1 the bending member 17 comprises a distal portion (designed 17') and a proximal portion (designed 17"). The distal portion 17' comprises a superelastic memory metal alloy that changes its shape from a stressed straight shape to an unstressed curved shape when deployed from the constraining housing 3. The rotating member 19 is in this case an integral cable extending through both sections 17' and 17" of the bending member. The rotating cable 19 is fixed to the clevis 11 (this fixture cannot be seen in FIG. 2 since it is hidden by the clevis 11.). Therefore it can cause the clevis 11 to rotate about its own axis, and also (as in FIG. 1) to rotate relative to the bending member 17. Thus, for example, with reference to FIG. 2 the clevis 11 can be made to slide circumferentially over the surface of bending member 17. It is not fixed thereto at the part 21 referenced in the drawings.

The rotating cable 19 can also serve as the activating cable to activate jaws 13, ie it can perform the function of both rotating member 7 and activating cable 15 of the embodiment of FIG. 1.

The embodiment of FIG. 2, like that of FIG. 1, therefore allows movement of the device in the plane of the paper (ie as indicated by arrow B) and in a perpendicular plane (as indicated by arrow C).

While the present invention has been shown and described with reference to preferred embodiments thereof it will be understood, by those skilled in the art, that the suggested variations and other changes in the form and detail of the devices may be made without departing from the scope and spirit of the invention.

We claim:

1. A surgical device comprising
   (a) a tubular housing having a longitudinal bore extending therethrough,
   (b) a first elongate member extending through the longitudinal bore of the housing, and having a proximal and distal segment, wherein at least part of the distal segment comprises an elastic material, and wherein the distal segment assumes a first shape when extended from the longitudinal bore, and bends to assume a second shape when withdrawn into the bore;
   (c) a second elongate member also having a proximal and distal segment, the second elongate member extending substantially parallel to the first elongate member so that it is bent by the first elongate member, when the first elongate member changes from its first to its second shape and vice versa, the second elongate member being rotatable relative to, and substantially about, the axis of the first elongate member, and
   (d) an operating head secured to the distal segment of the second elongate member sufficiently firmly so that it
      (i) is moved with the second elongate member when the first elongate member changes from its first to its second shape and
      (ii) can be rotated by the second elongate member relative to and substantially about the axis of the first elongate member.

2. A surgical device according to claim 1, wherein at least part of at least the distal segment of the second elongate member is tubular and surrounds at least part of the first elongate member.

3. A surgical device according to claim 2, wherein at least part of distal segment of the second elongate member is flexible.

4. A surgical device according to claim 2, wherein the proximal segment of the second elongate member can be moved from the proximal end of the housing to effect rotation of the operating head.

5. A surgical device according to claim 2, wherein the proximal segment of the second elongate member is also tubular and the tubular proximal segment is secured to the tubular distal segment of the second elongate member.

6. A surgical device according to claim 5, wherein the tubular proximal segment of the second elongate member projects from the end of the housing, and can be rotated by the operator of the surgical device to cause rotation of the operating head.

7. A surgical device according to claim 1, wherein at least part of at least distal segment of the second elongate member extends within at least part of at least the distal segment of the first elongate member.

8. A surgical device according to claim 7, wherein at least part of at least the distal segment of the first elongate member defines a tube.

9. A surgical device according to claim 8, wherein at least part of at least the distal segment of the first elongate member is a tube.

10. A surgical device according to claim 9, wherein the proximal segment of the first elongate member is also tubular.

11. A surgical device according to claim 8, wherein the second elongate member comprises a cable extending within the first elongate member.

12. A surgical device according to claim 1, wherein the said elastic material transforms from one shape to another without the application of heat.

13. A surgical device according to claim 1 wherein the said elastic material comprises a pseudoelastic shape memory alloy.

14. A surgical device according to claim 1 wherein the operating head comprises a holding means for holding a held article.

15. A surgical device according to claim 14, wherein the holding means is provided with a held article selected from the group consisting of jaws of a clamp, blades, scissors, and a needle.

16. A surgical device according to claim 14 comprising elongate activating means for activating the held article.

17. A surgical device according to claim 16 wherein the activating means passes through the outer of the first and second elongate members.

18. A surgical device according to claim 1, wherein the housing has a transverse dimension of less than 10 mm.

* * * * *